United States Patent
Bailey et al.

(10) Patent No.: US 7,815,433 B2
(45) Date of Patent: *Oct. 19, 2010

(54) ADJUSTABLE TOOL DRIVE ARRANGEMENT

(75) Inventors: Kevin John Bailey, Ottawa (CA); Andrew Douglas Millson, Ottawa (CA); Derek M. J. Turner, Ottawa (CA); Jean Castonguay, Hudson (CA)

(73) Assignee: TTI Turner Technology Instruments Inc., Ottawa, Ontario (CA)

( * ) Notice: Subject to any disclaimer, the term of this patent is extended or adjusted under 35 U.S.C. 154(b) by 394 days.

This patent is subject to a terminal disclaimer.

(21) Appl. No.: 11/262,959

(22) Filed: Nov. 1, 2005

(65) Prior Publication Data

US 2006/0281048 A1 Dec. 14, 2006

Related U.S. Application Data

(60) Provisional application No. 60/689,052, filed on Jun. 10, 2005.

(51) Int. Cl.
*A61C 1/14* (2006.01)

(52) U.S. Cl. ....................................... 433/129
(58) Field of Classification Search ......... 433/129–130; 279/43, 43.4, 43.2, 38
See application file for complete search history.

(56) References Cited

U.S. PATENT DOCUMENTS

| | | | | |
|---|---|---|---|---|
| 3,576,076 A | * | 4/1971 | Weissman | .................. 433/165 |
| 3,869,796 A | | 3/1975 | Thorburn | |
| 4,595,363 A | | 6/1986 | Nakanishi | |
| 4,710,075 A | * | 12/1987 | Davison | ..................... 408/202 |
| 5,040,980 A | | 8/1991 | Heil | |
| 5,275,558 A | | 1/1994 | Seney | |
| 5,549,474 A | | 8/1996 | Cohen | |
| 6,305,935 B1 | | 10/2001 | Cardarelli | |
| 6,575,747 B1 | | 6/2003 | Riitano et al. | |
| 2003/0230862 A1 | * | 12/2003 | Peters et al. | .................. 279/82 |

FOREIGN PATENT DOCUMENTS

| | | |
|---|---|---|
| CA | 2510722 A1 | 7/2004 |
| EP | 0 925 762 | 6/1999 |
| GB | 2 058 615 | 4/1981 |

OTHER PUBLICATIONS separate. (n.d.). Dictionary.com Unabridged (v 1.1). Retrieved May 29, 2009, from Dictionary.com website: http://dictionary.classic.reference.com/browse/separate.*

* cited by examiner

*Primary Examiner*—Cris L Rodriguez
*Assistant Examiner*—Heidi M Eide
(74) *Attorney, Agent, or Firm*—Clark Hill PLC (57) ABSTRACT

The invention relates to an improved dental tool drive arrangement for a handpiece with a drive head, the tool drive arrangement permitting length adjustment of the tool in the drive head by concentrically supporting the tool in the drive head at any position from a fully inserted position to a maximum retracted position. The tool drive arrangement preferably includes a tool and a rotatable tool supporting element for concentrically supporting the tool from the fully inserted to the maximum retracted position, the tool preferably including a maximum retraction indicator for indicating to a user when the tool has been retracted to the maximum retraction position. This provides a significant advantage over the prior art by allowing a user to adjust the exposed length of a rotatable tool, preferably a dental bur, without exceeding safe operating limits. The invention also relates to an improved drive spindle which allows depth adjustment of a tool in a dental handpiece while maintaining efficient torque transfer and concentricity during high speed rotation.

12 Claims, 9 Drawing Sheets

ADJUSTABLE TOOL DRIVE ARRANGEMENT

CROSS-REFERENCE TO RELATED APPLICATION

This application claims priority from U.S. Application Ser. No. 60/689,052, entitled Dental Burr And Drive Spindle, filed Jun. 10, 2005, which application is included herein by reference in its entirety.

FIELD OF THE INVENTION

The present invention relates generally to handpieces for rotating tools. More particularly, the present invention relates to an improved drive arrangement for a rotatable tool, including a drive spindle and the tool.

BACKGROUND OF THE INVENTION

Numerous handpieces for rotating tools exist. Turbine driven handpieces are widely used in dental offices and medical labs around the world. Most handpieces include a handle and drive head for supporting the rotating tool. A connector, often a swivel connector, connects the handpiece to various air, water, light and power supply conduits, generally combined in a so-called umbilical cord. The drive head houses a tool drive arrangement, generally composed of a tool retaining mount or chuck, and a motor or turbine, rotatably mounted in the head for driving the chuck. The chuck releasably holds the tool, such as a dental bur, for rotation about an axis of rotation.

In known handpieces, the tool is releasably held by the chuck against axial movement in the drive arrangement. Screw lock or pushbutton lock arrangements are provided for the manual locking and releasing of the tool in and from the chuck. The known drive arrangements are not designed to allow for length adjustment of the tool, which means the tool, once fully inserted in the drive arrangement will always protrude the same length from the drive head. However, as a dental procedure progresses, a dentist may need to use dental tools of different length. This creates the need for repeated tool changes, which is time consuming and cost intensive, since a collection of different length tools must be purchased.

In an attempt to find a time and cost efficient solution, dentists often try to adjust the protruding length of the bur by somewhat retracting the bur from the drive head until the desired length is reached. However, this adjustment is made without knowledge whether the bur will remain properly engaged within the drive mechanism and safely secured within the drive head. This is a dangerous practice, since prior art handpieces are not designed to hold the bur in any position other than fully inserted into the drivehead. The tool when retracted may remain within the drive head in the prior art handpieces due to the retaining force of the friction arms normally included in the chuck. However, concentrical support of the tool within the drive head and reliable torque transmission from the drive to the tool are not ensured.

Conventional handpiece designs provide for concentrical support of the tool in the fully inserted condition. Support is provided at a rear, inserted end of the tool and at an intermediate location of the tool corresponding to the area of the bottom bearing in the drivehead. However, upon even a minor retraction of the tool from the fully inserted position, the tool is disengaged from the concentrical support at the rear end of the tool. The tool must then be maintained in axial alignment with the rotating drive by way of the friction arms of the chuck. However, those friction arms are somewhat flexible by design and generally do not provide sufficient force to maintain the rear end of the tool concentrically aligned in the drive when lateral forces are applied to the working end of the tool during use. Therefore, operation of a conventional handpiece at a tool insertion depth other than fully inserted can result in loss of concentricity, vibration of the bur during rotation, excessive wear, damage to the drive assembly, permanent deformation of the tool securing mechanism and drive spindle components, inefficient torque transfer, increased bur slippage (both rotational and axial), and most dangerously, accidental disengagement of the bur from the handpiece during use.

Therefore, a need exists for a dental tool and handpiece design allowing for tool depth adjustment without a loss of concentricity.

Prior art chucks of dental handpieces are almost exclusively designed to hold the dental bur by way of friction fit only. Examples of such constructions are found in U.S. Pat. No. 3,869,796, U.S. Pat. No. 4,595,363, U.S. Pat. No. 5,275,558, and U.S. Pat. No. 5,549,474. Only low torque transmission is possible between the chuck and the bur in such constructions, higher torque leading to slippage of the bur. At the high rotational speeds achieved by modern dental handpieces, bur slippage, in both the axial and rotational directions, can become a problem. Rapid deceleration of the bur can also lead to rotational slippage, for example, when the drive continues to rotate while the bur is locked or snagged. Friction between the drive assembly and the dental bur during rotation leads to significant wear of both elements over time. This friction can also produce significant heat, as can friction generated in push-button lock handpieces when the user maintains pressure on the push-button during operation. Friction heat can cause permanent damage to the drive spindle components, especially the flexible friction arms of the chuck, which are normally made of heat tempered material. The damage can lead to rotational slippage and even axial slippage of the tool, possibly resulting in an accidental release of the tool from the handpiece. Accidental release of a dental bur during high speed rotation can pose a threat to both the patient and the dentist. Continued wear of the bur and drive assembly during operation necessitates routine maintenance and repair of expensive handpiece components.

Thus, a drive spindle design is desired which not only allows for adjustment of the exposed tool lengths and preferably also prevents rotational slippage of the tool at all possible tool retraction positions to avoid frictional wear and resulting heat damage to the drive spindle.

SUMMARY OF THE INVENTION

It is an object of the present invention to obviate or mitigate at least one disadvantage of prior art handpiece designs.

In a first aspect, the invention provides a tool drive arrangement for a handpiece with a drive head, the tool drive arrangement permitting length adjustment of the tool in the drive head by concentrically supporting the tool in the drive head at any position from a fully inserted position to a maximum retracted position.

In a preferred embodiment, the tool drive arrangement includes a tool and a rotatable tool supporting element for concentrically supporting the tool from the fully inserted to the maximum retracted position, the tool including a maximum retraction indicator for indicating to a user when the tool has been retracted to the maximum retraction position. This provides a significant advantage over the prior art by allowing a user to adjust the exposed length of a rotatable tool, preferably a dental bur, without exceeding safe operating limits.

In a preferred embodiment of the tool, the tool includes a tool body having an axis of rotation, the tool body being divided into a driven portion with a driven end for insertion into the tool supporting element, and a working portion for projection from the drive head during use. The tool further includes a maximum retraction indicator on the driven portion for indicating to a user when the tool is retracted from the fully inserted position to the maximum retraction position.

In another preferred embodiment, the tool supporting element is a drive spindle for concentrically supporting the tool at different insertion depths from a maximum insertion depth at the fully inserted position to a minimum insertion depth at the maximum retraction position. The drive spindle includes a drive torque receiving portion, a tool supporting portion with a tool passage for receiving the driven portion of the tool and a tool retaining member for releasably retaining the driven portion in the tool passage. The tool supporting portion includes a first tool seat for supporting the drive end of the tool and a second tool seat for supporting the driven portion at a location intermediate the driven end and the working portion of the tool. The first seat has a sufficient axial length for concentrically supporting the driven end when the tool is retracted from the fully inserted position to a retracted position wherein the retaining member still engages the driven portion.

In one aspect, the maximum retraction indicator is a visible indicia located on the driven portion, intermediate the driven end and the working portion, to be hidden from view when the tool is inserted at a depth between the maximum and minimum insertion depth and visible to a user when the tool is retracted from the drive head to the maximum retraction position or further. Preferably, the maximum retraction indicator is selected from the group of at least one dot, line, colored line, etched line, line having a surface roughness different from the remainder of the driven portion, a change in diameter of the tool and a groove. The line or groove can be continuous or broken, such as a line of dots. The line or groove can extend in circumferential or longitudinal direction of the tool or at any angular orientation therebetween. The maximum retraction depth can be indicated by an end or an edge of the line or groove. The maximum retraction depth can also be indicated by a change in the overall appearance of the line or groove, such as a change in color, a change in size, a change in any other characteristic, or any combination thereof.

In another aspect, the maximum retraction indicator is a mechanical indicia located on the driven portion for engagement by a portion of the tool supporting element when the maximum retraction depth is reached. Preferably, this mechanical engagement provides a tactile indication to the user that the maximum retraction depth is reached. In a preferred embodiment, the mechanical indicia is a stop on the driven portion of the tool for mechanical interaction with the tool retaining member of the tool supporting element when the tool is retracted to the maximum retraction depth. Preferably, the tool supporting element includes a tool retaining member for frictionally retaining the tool and the tool further includes a contact surface on the driven portion for engagement by the tool retaining member at insertion depths from the maximum insertion depth to at least the minimum insertion depth;

the stop being a stop shoulder on the contact surface for axial engagement by the tool engaging member when the tool is retracted from the maximum insertion depth to the maximum retraction position.

In one variant, the contact surface is a detent on the driven portion and the stop is an axial end shoulder of the detent. In a particularly preferred embodiment, frictional engagement of an elongated detent by the tool retaining member allows the tool to be positioned in the handpiece at any insertion depth between the minimum insertion depth and the maximum insertion depth. In another variant, the tool comprises two or more detents on the driven portion, each having a stop shoulder for axial engagement with the tool engaging member for defining one or more intermediate insertion depths between the minimum tool insertion depth and the maximum retraction position. In a particularly preferred embodiment, the detent is a groove extending circumferentially about the driven portion of the tool.

Those skilled in the art will appreciate that the tool insertion depth indicator and tool retaining member can be achieved by other means than those described in the preferred embodiments of the invention without deviating from the essence of the invention. It will also be apparent that more than one tool retaining member can be provided in the tool supporting element while preserving the core function.

It is a significant advantage of an adjustable length tool drive arrangement in accordance with the invention allowing axial adjustment of a dental tool insertion depth in a dental handpiece that the number of times a dentist must exchange tools for selection of different tool lengths during the course of a dental procedure is reduced. This reduces the time required to perform the procedure and can reduce operating cost, since fewer tools of specific length need to be purchased and maintained. It is another significant advantage that by providing the preferred maximum retraction indicator excessive wear and damage due to insufficient insertion of the tool in the handpiece are avoided.

In an alternate embodiment, the minimum tool insertion depth indicator is a combination of a mechanical and a visual indicator.

In a preferred embodiment of the tool supporting element, the drive spindle has a chuck including the tool supporting portion and the tool retaining member. The tool passage is an axial bore in the chuck for receiving the driven portion of the tool up to a maximum insertion depth at which depth the tool is fully inserted into the spindle. The tool retaining member is a resilient tool engaging member for releasably frictionally engaging a contact surface on the driven portion of the tool from an engagement depth, at which depth the contact between the tool engaging member and the driven portion is initiated during tool insertion, to the maximum insertion depth. In a preferred embodiment, the tool engaging member is shaped and constructed to axially engage a maximum retraction depth indicator on the tool in the form of a stop shoulder on the contact surface, when the tool is retracted from the maximum insertion depth to a maximum retraction depth found between the maximum insertion depth and the engagement depth. The tool engaging member is shaped and constructed to frictionally engage the driven portion to prevent axial movement of the tool in the spindle during operation of the handpiece.

In a preferred embodiment, the chuck is a generally cylindrical member having the tool receiving axial bore. A portion of the wall surrounding the bore is resiliently deformable and forms the resilient tool engaging member to allow insertion of the driven portion of the tool into the bore. When the tool is inserted, the wall portion radially inwardly engages the driven portion to frictionally retain the tool in the bore. Axial engagement of the tool engaging member with a first stop shoulder on the contact surface provides a maximum tool retraction indication.

In a particularly preferred embodiment, the resilient wall portion is in the form of a pair of diametrically opposed axially extending retaining arms each having a radially inwardly projecting protrusion for frictionally engaging the contact surface of the tool and for axially engaging a mechanical maximum retraction depth indicator on the tool. In a particularly preferred embodiment, the drive spindle of the present invention further comprises a ram for selectively forcing apart the retaining arms to allow insertion and/or removal of the tool. The ram is preferably axially aligned with and adjacent the chuck in the drive spindle, and operatively engages the chuck for transfer from the drive. In a particularly preferred variant, a hollow cylindrical sleeve is provided for supporting the chuck and the ram in this axially aligned configuration.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein.

DETAILED DESCRIPTION OF THE PREFERRED EMBODIMENTS

Generally, the present invention provides a tool drive arrangement for a handpiece with a drive head, the tool drive arrangement permitting length adjustment of a tool in the drive head by concentrically supporting the tool in the drive head at any position from a fully inserted position to a maximum retracted position.

In one embodiment, the tool drive arrangement includes a tool and a rotatable tool supporting element for concentrically supporting the tool from the fully inserted to the maximum retracted position. The tool includes a maximum retraction indicator for indicating to a user when the tool has been retracted to the maximum retraction position. This provides a significant advantage over the prior art by allowing a user to adjust the exposed length of a rotatable tool, preferably a dental bur, without exceeding safe operating limits.

More particularly, the rotatable tool drive arrangement in accordance with the invention includes a rotatable tool; and a tool supporting element for releasably supporting the tool. The tool supporting element is insertable into a drive head for coaxial rotation in the drive head. The tool has a tool body having an axis of rotation and being divided into a driven portion with a driven end for insertion into the tool supporting element and a working portion for projecting from the drive head during use. The tool supporting element has a tool passage for coaxially receiving the driven portion of the tool at different insertion depths, the tool passage including a first tool seat for concentrically supporting the driven end of the tool and a second tool seat for concentrically supporting the driven portion at a location intermediate the driven end and the working portion. The first tool seat is axially elongated for concentrically supporting the driven end at any position from a maximum insertion position wherein the tool is fully inserted into the tool passage to a maximum retraction position wherein the tool is retracted from the maximum insertion position.

The invention will now be described in more detail with reference to a specific preferred embodiment of the invention directed to an improved tool drive arrangement wherein the tool is a dental tool, such as a bur, and the tool supporting element is a drive spindle, such as a drive spindle for use in high speed dental handpieces. Although specific reference is made in the following to a dental bur and a drive spindle for a high speed dental handpiece, it will become apparent to those skilled in the art that all structural and functional features of the invention are equally applicable to rotatable dental and medical tools in general and to medical and dental handpieces and other handpieces for supporting high speed rotating tools.

Figure 1:
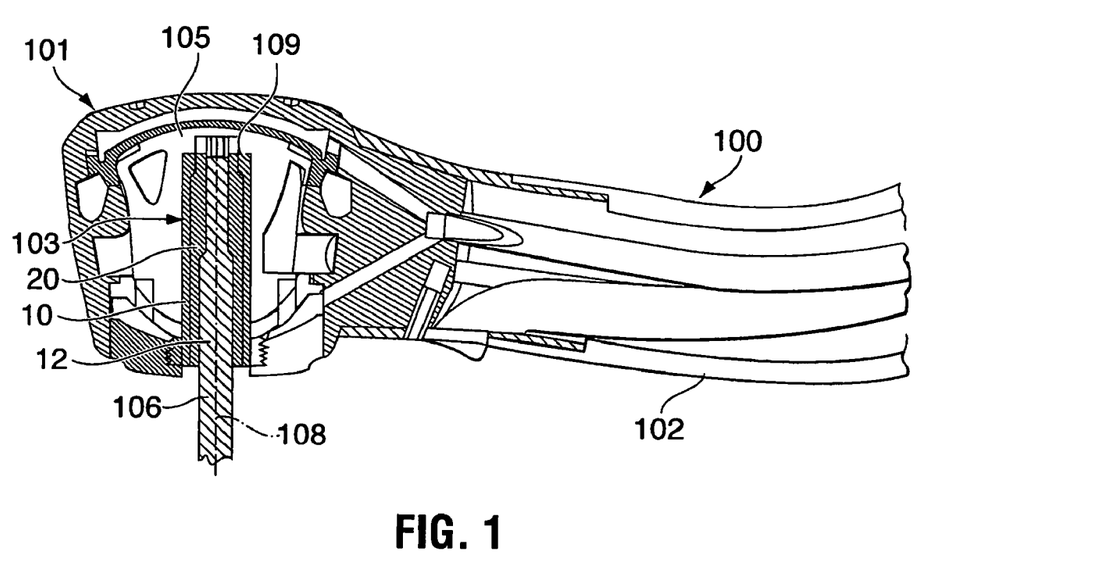
FIG. 1 is a cross-sectional view of a dental handpiece including a tool drive arrangement in accordance with one preferred embodiment of the present invention.

A high speed dental handpiece 100, as shown in FIG. 1 generally includes a handle 102, a tool supporting drive head 101, and a swivel connector (not illustrated) for connecting the handpiece to various air, water, light and power supply conduits, generally combined in a so called umbilical cord (not shown). The drive head 101 includes a torque producing drive 105, typically a motor or turbine rotatably mounted in the drive head, and having a spindle socket 109 for housing a tool supporting element 103, here a drive spindle 10. The tool supporting element 103 typically includes a tool receiving and retaining portion, here a chuck 20, constructed to releasably retain a tool 106, such as a dental bur, for rotation about an axis of rotation 108.

Referring now to FIGS. 1 to 3E, a dental tool 106 such as the dental bur 50 shown in FIGS. 3A to 3E typically has an elongated body 52 divided into a generally cylindrical driven portion 54 for insertion into the drive head 101 of a dental handpiece 100 for receiving drive torque from the drive 105 of the handpiece, and a working portion 56 for projecting from the drive head 101 of the handpiece in an operating condition. The working portion has a working end 58 for engagement with a working surface, such as a tooth surface (not illustrated) during a dental procedure. The user, typically a dentist, must purchase a collection of burs varying in shaft length as well as structure of the working end 58 of the working portion 56. The dental bur 50 is generally inserted into the spindle 10 in the drive head 101 and is removably supported therein by the chuck 20 for rotation with the spindle 10 about the axis of rotation 108.

Figure 2:
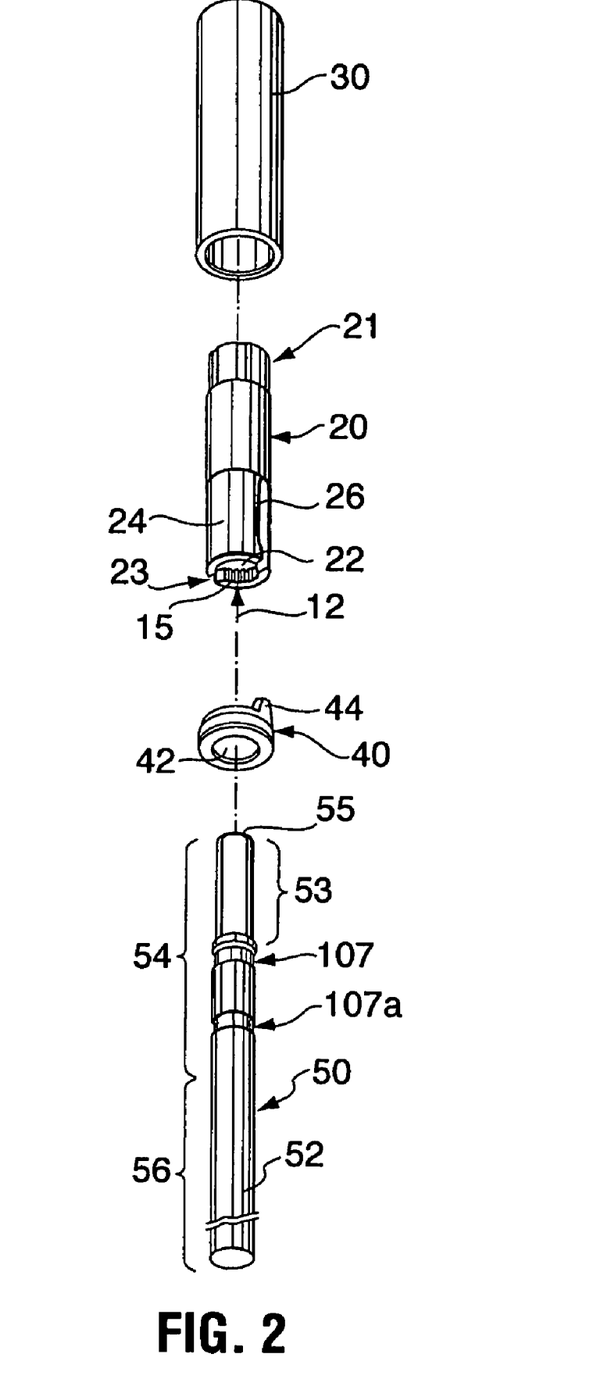
FIG. 2 illustrates a perspective view of the tool and drive spindle components of the preferred tool drive arrangement shown in FIG. 1.

As illustrated in FIG. 2, a preferred embodiment of the tool aspect of the present invention provides an improved dental bur 50, preferably for use with an improved drive spindle 10 to be described in more detail below.

Different preferred embodiments of the tool aspect of the present invention are now described by reference to the various preferred dental bur embodiments shown in FIGS. 3A to 3E. The dental bur 50 illustrated in FIGS. 3A to 3E includes a body 52 having an axis of rotation 52*a*, a working portion 56 for projecting from the drive head 101 (see FIG. 1) during use, and a driven portion 54 for insertion into the drive head for directly or indirectly receiving drive torque. All illustrated burs include a maximum retraction indicator 107, which can be either a visible indicator 57 as shown in the burs of FIGS. 3A to 3C, a mechanical indicator 59 as shown in the bur of FIG. 3D, or a combination visible/mechanical indicator as shown in FIG. 3E.

Figures 3A, 3B, 3C, 3E:
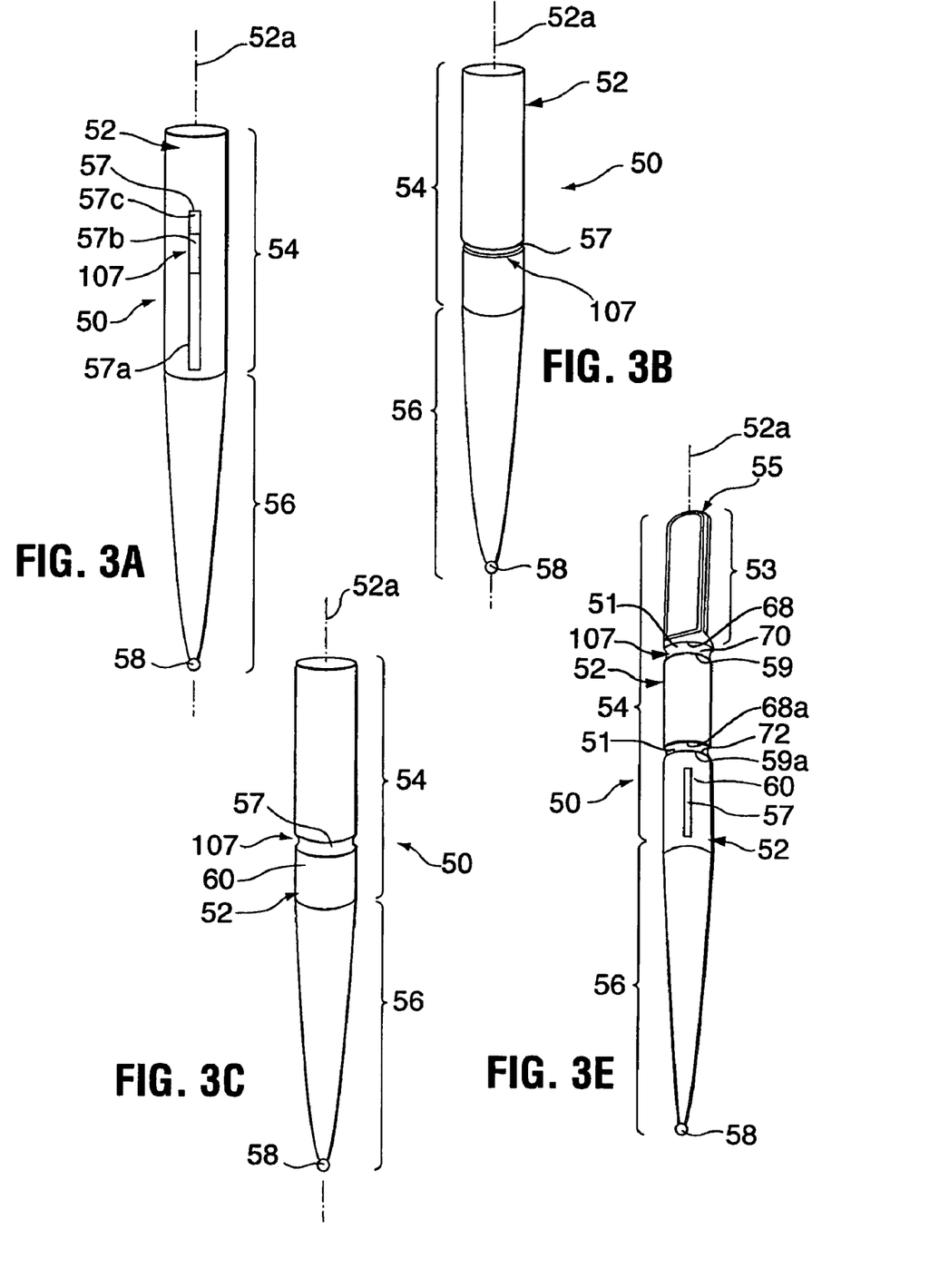
FIGS. 3A to 3E show perspective views of dental tools including different types of maximum retraction indicators in accordance with various preferred embodiments of the tool aspect of the invention.

The visible indicator 57 of the burs of FIGS. 3A to 3C and 3E is provided on or in the surface of the driven portion 54 of the bur 50 such that the indicator is not visible at the maximum tool insertion depth. When the driven portion 54 is retracted from the maximum insertion depth toward the maximum retraction depth for depth adjustment, the visual indicator 57 becomes apparent to the user, preferably only when the maximum tool retraction position or minimum tool insertion depth is reached. A few examples of visual indicia include, but are not limited to, a dot, a line, a colored line, an etched line, a line having a surface roughness different from the remainder of the driven portion, a detent and a groove. The visual indicator 57 can extend circumferentially about the driven portion 54 as shown in FIG. 3B, axially along the driven portion 54 as shown in FIG. 3A and at an angular orientation to the axis of rotation 108 (not shown). If the visible indicator 57 extends axially as shown in FIG. 3A, the maximum retraction position can be indicated by the start or end of the indicator, by an edge of the indicator, or by a change in the overall appearance of the indicator, such as a change in color, a change in size, a change in any other characteristic, or any combination thereof. This is shown in FIG. 3A which illustrates a bur 50 with a visual indicator 57 having sections 57*a* to 57*c* of different characteristics (preferably colour), whereby the maximum extraction depth is indicated by the transition from section 57*b* to section 57*c* becoming visible to the user.

The bur of FIG. 3D has a contact surface 60 on the driven portion 54 for frictional engagement by a tool engaging member 15 of the spindle 10 to be discussed in more detail below in relation to FIG. 2. The tool engaging member engages the contact surface 60 at insertion depths of the tool from an engagement depth, at which contact between the tool engaging member 15 and the driven portion 54 is initiated, to a maximum insertion depth, at which the bur 50 is fully inserted into the handpiece 100. The mechanical type maximum retraction indicator 59 includes a first stop shoulder 68 on the contact surface 60 for axial engagement with the tool engaging member 15 when the bur 50 is retracted from the maximum insertion depth to a maximum retraction depth between the engagement depth ($D_{min}$) and the maximum insertion depth ($D_{max}$) (see FIGS. 10 and 11).

Figure 3D:
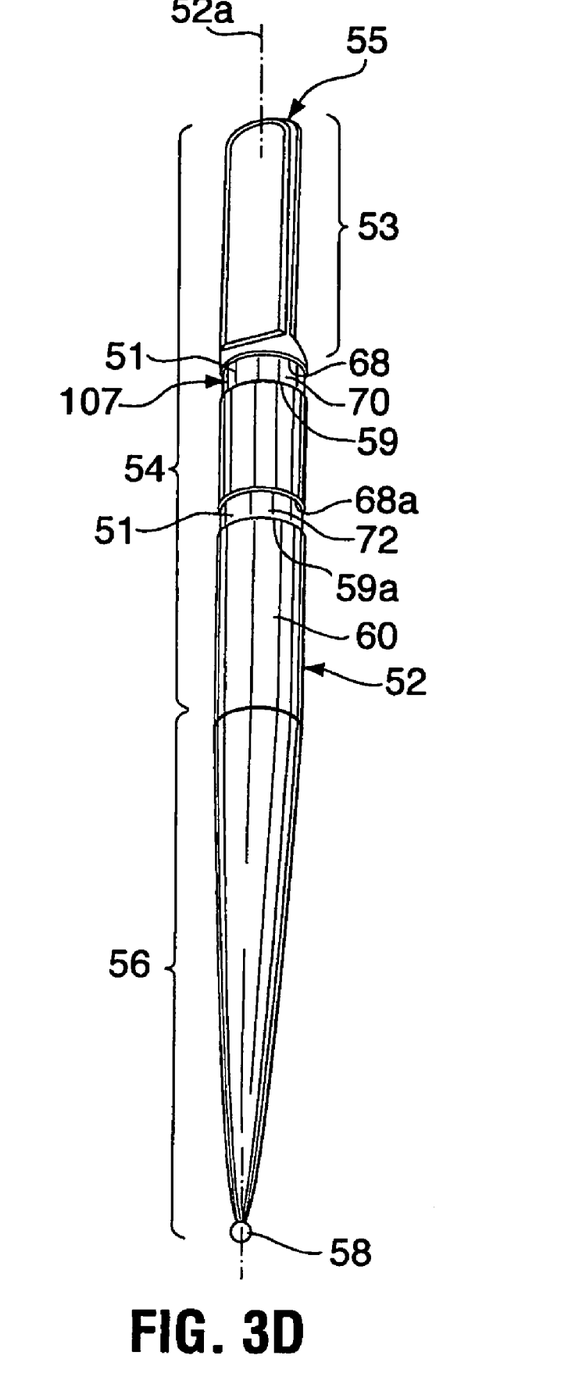

The bur of FIG. 3E includes both the visible indicator 57 shown in FIG. 3B and the mechanical indicator 59 shown in FIG. 3D.

In a preferred embodiment as shown in FIG. 2, the mechanical type maximum extraction indicator 59 is a detent 51 located on the driven portion 54, the detent having the first axial stop shoulder 68 for axial engagement by the tool engaging member 15 of the drive spindle 10 for indicating the maximum retraction depth or minimum insertion depth ($D_{min}$) of the bur 50 in the drive spindle 10. $D_{min}$ is essentially the depth at which the working portion 56 is maximally extended from the handpiece while the driven portion 54 is still concentrically supported in the drive spindle 10 and properly engaged with the drive mechanism in the handpiece for reliable torque transfer. $D_{min}$ can be easily determined for various handpiece and spindle designs without undue experimentation. A more conservative $D_{min}$ can be selected which is greater than the depth at which the working portion 56 is maximally extended from the handpiece. The difference between $D_{min}$ and $D_{max}$ provides a length of axial play along which the bur 50 can be safely adjusted in the drive spindle 10.

As illustrated in the preferred embodiment shown in FIG. 2, a second retraction depth indicator 107*a* can be provided on the driven portion 54 for defining a corresponding intermediate insertion depth of the driven portion 54 in the drive spindle 10 between $D_{min}$ and $D_{max}$. The preferred embodiment illustrated in FIG. 3D shows two annular circumferential detents 51 on the driven portion 54, those being the maximum retraction depth indicator 59 and an intermediate insertion depth indicator 59*a*, having first and second stop shoulders 68 and 68*a* respectively for axial engagement with the tool engaging member 15 upon retraction (see FIG. 2) of the driven portion 54 from the maximum insertion depth toward the intermediate insertion depth, $D_{min}$ or the engagement depth. Axial engagement of the first axial stop shoulder 68 by the tool engaging member 15 indicates that $D_{min}$ is reached. In the variant shown in FIG. 3D, axial engagement of the second stop shoulder 68*a* by the tool engaging member 15 occurs when the tool is inserted to essentially $D_{max}$ (see FIG. 10). The second stop shoulder 68*a* thus serves to retain the driven portion 54 at $D_{max}$ during operation of the handpiece, while the first stop shoulder 68 serves to retain the driven portion 54 at $D_{min}$ during operation with a maximally extended bur 50 (see FIG. 11).

Figure 5:
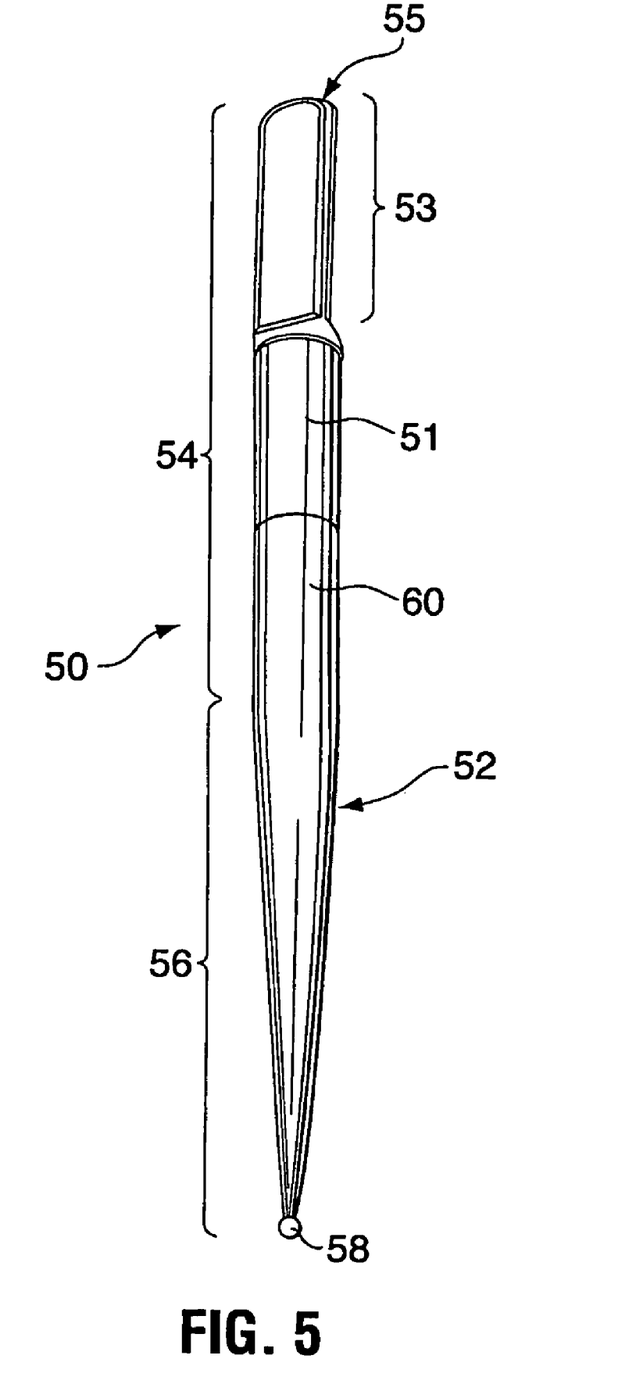
FIG. 5 illustrates a perspective view of a preferred embodiment of a dental bur type tool of the invention having a mechanical maximum retraction indicator in the form of a single, axially elongated detent for continuous depth adjustment.

Alternative embodiments of the mechanical tool insertion depth indicator of the present invention include, but are in no way limited to: (a) a single axially elongated detent 51 on the driven portion 54 as illustrated in FIG. 5, for continuous depth adjustment, wherein frictional engagement of the contact surface 60 of the detent 51 by the tool engaging member 15 allows the tool to be securely positioned in the handpiece at any insertion depth between $D_{min}$ and $D_{max}$ during operation of the handpiece, $D_{min}$ being indicated by axial engagement of the first stop shoulder 68 by the tool engaging member 15; (b) a plurality of insertion depth indicators 59 as shown in FIG. 3D, each having a stop shoulder 68 located on the driven portion 54 for defining a plurality of corresponding intermediate insertion depths between $D_{min}$ and $D_{max}$, $D_{min}$ being indicated by the first axial stop shoulder 68 of the maximum retraction depth indicator 59; (c) a contoured annular maximum retraction depth indicator that gradually tapers radially outward axially from the first stop shoulder in the direction of the working portion 56 (not illustrated), wherein frictional engagement of the contact surface of the tapered annular detent by the tool engaging member 15 allows the driven portion 54 to be positioned in the handpiece at any insertion depth between $D_{min}$ and $D_{max}$, $D_{min}$ being indicated by the first axial stop shoulder 68.

Although for ease of manufacture the mechanical indicator 59 described above is preferably in the form of a recessed detent 51 on the contact surface 60 of the driven portion 54, it will be readily understood that the indicator, and especially the stop shoulder 68, could also be in the form of an elevation protruding from the surface of the driven portion 54.

A preferred detent is any type of recess located on the body 52 of the bur 50, but is preferably an annular, circumferentially extending groove on the driven portion 54. An axially elongated detent or a plurality of axially spaced apart detents on the driven portion 54 can allow for axial adjustment of the bur 50 in the drive spindle 10 at a range of depths between $D_{min}$ and $D_{max}$, and thereby provide for "depth indexing". Operation of the handpiece at tool insertion depths between $D_{min}$ and the engagement depth is possible due to frictional engagement of the driven portion 56 by the tool engaging member 15 but is not preferred due to the disadvantages associated with bur overextension.

In a preferred embodiment of the present invention as illustrated in FIGS. 1, 2, 6A, 6B and 7 to 11, the tool supporting element, in this embodiment the spindle 10, is insertable into the spindle socket 109 of the drive head 101 for coaxial rotation in the drive head. The tool 106, here the bur 50, has the tool body 52 with axis of rotation 108, the driven portion 54 with driven end 55 for insertion into the spindle 10 and the working portion 56 for projecting from the drive head during use. The spindle 10 has a tool passage 12 for coaxially receiving the driven portion 54 of the tool at different insertion depths, the tool passage 12 including a first tool seat or first bur seat 14 for concentrically supporting the driven end 55 of the bur 50 and a second tool seat or second bur seat 16 for concentrically supporting the driven portion 54 at a location intermediate the driven end 55 and the working portion 56 (see FIGS. 10, 11). The first tool seat 14 is axially elongated for concentrically supporting the driven end 55 at any position from a maximum insertion position wherein the bur 50 is fully inserted into the tool passage 12 (see FIG. 10) to a maximum retraction position (see FIG. 11), wherein the bur 50 is retracted from the maximum insertion position. In a preferred embodiment of the first tool seat 14, the axial length (depth) of the first tool seat is at least equal to 10% of the axial length of the driven portion 54 of the bur 50 used in combination with the spindle 10. To obtain a sufficiently large retraction length, the axial length (depth) of the first tool seat 14 is more preferably at least 15% of the axial length of the driven portion 54, most preferably at least 20%. Practical retraction ranges are achievable when the axial length (depth) of the first tool seat 14 is 15 to 60% of the axial length of the driven portion 54, more preferably 20 to 75%, although other length ratios are also within the confines of the present invention. The axial length of the first tool seat 14 can also be selected independent of the length of the driven portion 54 of the bur 50 used in combination therewith, preferred seat lengths being at least 1.5 mm, more preferably at least about 2 mm, more preferably about 2-7 mm and most preferably about 5 mm.

The spindle 10 of the preferred embodiment of the tool supporting element (as shown in FIGS. 9A, 9B, 10, 11) includes a torque receiving element in the form of a generally cylindrical casing sleeve 30 which fits into the spindle socket 109 of the drive head 101 for receiving rotational torque from the drive 105. The casing sleeve 30 houses a tool supporting element in the form of a chuck 20 for releasably supporting the bur 50 and a ram 40 for selectively releasing the bur 50 from the chuck 20. The chuck 20 includes the tool passage 12 in the form of a tool receiving axial bore 22 for receiving the driven portion 54 of the bur 50 coaxial with the axis of rotation 108. The axial bore preferably extends from a driven chuck end 21 of the chuck 20 to the tool receiving end 23. The chuck 20 further includes a tool retaining member 104 in the form of a resilient tool retaining arm 24. The tool passage 12 includes the first tool seat 14 for supporting the driven end 55 of the bur 50 and the second tool seat 16 for supporting the driven portion 54 at a location intermediate the driven end 55 and the working portion 56. The first tool seat 14 has a sufficient extent in axial direction (sufficient depth) to concentrically support the driven end 55 even when the tool is retracted from the maximum insertion depth $D_{max}$ at which the driven portion 54 is fully inserted into the tool passage 12 to a retracted position at which the tool retaining member 15 still engages the driven portion 54.

The tool retaining arm 24 is formed by a resilient portion of the wall 13 surrounding the axial bore 22. The retaining arm 24 is preferably radially resiliently deflectable for insertion of the driven portion 56 into the bore 22. The retaining arm 24 has a tool engaging tab 25 for contact with the contact surface 60 of the bur 50. The retaining arm is made of a sufficiently strong material (preferably stainless steel) to bias the tool engaging tab 25 against the contact surface 60 with sufficient force, once the driven portion 54 was inserted into the axial bore 22, to frictionally engage the bur 50 for torque transfer and to prevent axial movement of the bur 50 in the drive spindle 10 during operation of the handpiece 100. The selection of appropriate materials for the chuck 20 and the retaining arm 24 is not part of the present invention and well within the abilities of the art skilled person. It will also be readily apparent to the art skilled person that the chuck 20 may be provided with multiple retaining arms 24, such as the pair of diametrically opposite retaining arms 24 shown in the embodiment of FIGS. 2, 6A, 6B, 10 and 11. The retaining arm 24 preferably extends towards the tool receiving end 23 of the chuck 20 (see FIGS. 10 and 11) and the tool engaging member 15 is preferably located near the tool receiving end 23 for frictional engagement with the driven portion 56. This allows for a much larger retraction range than with a retaining arm 24 extending towards the driven chuck end 21 of the chuck 20, since the bur 50 at maximum retraction must still be held by the retaining arm.

Figure 10:
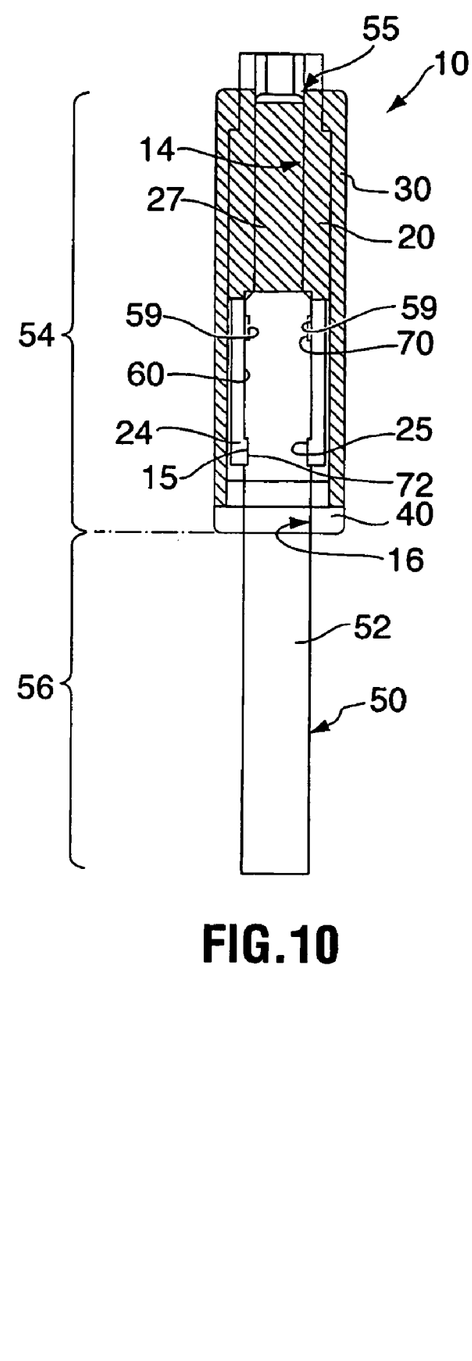
FIG. 10 illustrates an axial cross-section through the drive spindle of FIG. 2, but in an assembled condition and with a dental tool as shown in FIG. 3D inserted into the spindle to the maximum insertion depth.
Figure 11:
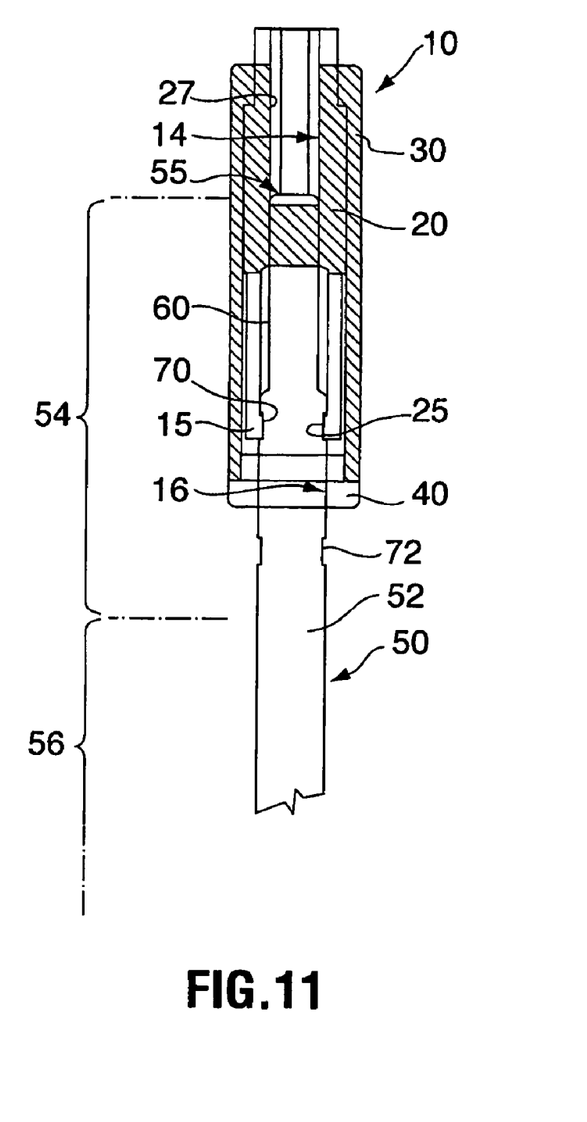
FIG. 11 illustrates the assembled drive spindle and dental tool combination shown in FIG. 10 with the tool retracted to the maximum retraction length.

In the embodiment of the tool drive arrangement of the invention shown in FIGS. 10 and 11, the chuck 20 is constructed for interaction with the mechanical maximum extraction indicator 59 on the bur 50 to indicate $D_{min}$. To that end, the tool engaging tab 25 protrudes radially inwardly from the retaining arm 24 and is sized and shaped to not only fit into the mechanical maximum extraction indicator 59, in this embodiment an indicator groove 70, but to also generate a tactile sensation for the user to indicate that $D_{min}$ has been reached. In this manner, the user can insert the bur 50 into the chuck 20 until $D_{max}$ is reached, which is apparent from the fact that no further insertion of the bur is possible, and then retract the bur 50 to the desired position. Over-retraction of the bur 50 from the chuck 20 is prevented by the tactile sensation of the tool engaging tab 25 snapping into the indicator groove 70 which is felt by the user when $D_{min}$ is reached. Engagement of the tool engaging tab 25 on the retaining arm 24 with the indicator groove 70 also provides an additional safety feature not available in conventional handpiece designs. ISO recognizes excessive heat as one of the major contributing factors to chuck fatigue and failure in conventional handpieces. To avoid the generation of excessive heat by the user maintaining pressure on the bur release push button of a turbine handpiece, one of the ISO standards stipulates the minimum set back force of the push button resetting spring. The intention of that standard is to avoid friction between the push button mechanism and the spindle of the handpiece during rotation of the turbine. Excessive heat not only reduces lubrication, but more importantly can lead to relaxation of the spring force of the bur retaining arms of the chuck. Those arms are generally made of tempered steel and excessive heat leads to creep of the tempered material, thereby relaxing their resetting force. Once relaxation has occurred, the bur may no longer be reliably retained in the chuck. This problem is overcome with the embodiment of the tool drive arrangement of the invention shown in FIGS. 10 and 11, wherein the tool engaging tab 25 on the retaining arm 24 engages the indicator groove 70. This mechanical engagement can be achieved even after heat relaxation of the retaining arm 24, so that the bur 50 is more reliably retained in the chuck 20.

In one variant as illustrated in FIGS. 10 and 11, the bur 50 includes the indicator groove 70 as well as a maximum insertion groove 72 into which the tool engaging tab 25 snaps when the bur 50 is fully inserted into the chuck 20. This provides a tactile sensation to the user at both maximum insertion and maximum retraction of the bur. In another variant (not illustrated), the bur 50 in addition to the indicator groove 70 and the maximum insertion groove 72 includes one or more intermediate insertion grooves (not shown) located therebetween which each cooperate with the tool engaging tab 25 to provide a tactile sensation to the user. These additional grooves can be spaced along the driven portion 54 at selected intervals to provide a 'depth indexing' or 'retraction length indexing' function. In yet a further variant (not illustrated), the multiple annular indexing grooves can be replaced with a helical indexing groove extending along the driven portion 56 or the bur 50, allowing for depth indexing of the bur by rotating the bur 50 relative to the chuck 20 while the tool engaging tab 25 is engaged in the helical groove. Multiple helical grooves can also be provided.

In a particularly preferred embodiment (see FIGS. 9A, 9B), the chuck 20 includes a pair of diametrically opposed retaining arms 24 formed by two semi-circular wall portions of the chuck 20 which are separated by axial slits 26. The tool engaging tab 25, as seen in FIG. 6, is formed by one or more protrusions extending radially inward from an inner surface of the retaining arms 24 about the central axis 29 for frictionally engaging the contact surface 60 of the driven portion 56 to prevent axial movement of the bur 50 during operation of the handpiece 100, and for axial engagement with the first axial end shoulder 68 of the maximum retraction indicator 59 (see FIG. 2) for indicating $D_{min}$ is reached.

In another variant, the tool engaging tab 25 is formed by a pair of diametrically opposed annular ridges (FIG. 12) protruding from the inner surfaces of two opposed semi-circular retaining arms 24. The retaining arms and tool engaging tabs can be constructed and achieved by any means known to those skilled in the art.

Figure 9A:
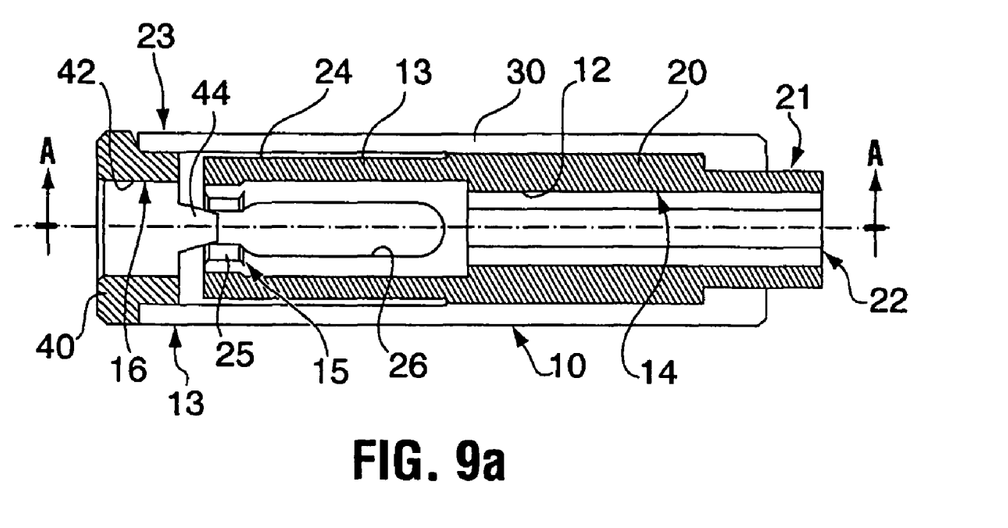
FIGS. 9A and 9B illustrate axial cross-sections of the drive spindle of FIG. 7 taken along lines A-A and B-B in FIG. 7, respectively.
Figure 9B:
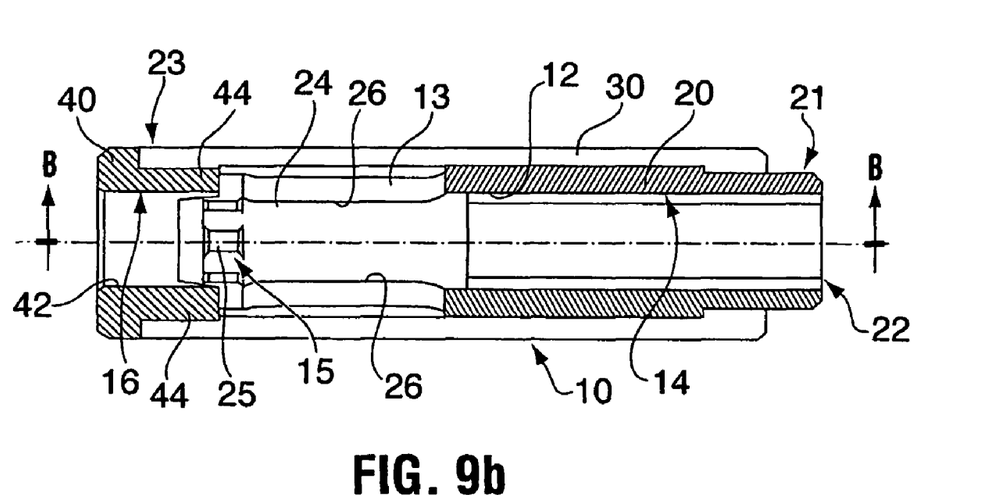

In the embodiment of the tool drive arrangement shown in FIGS. 2, 9A, 9B, the drive spindle 10 further includes a ram 40 for radially forcing apart the retaining arms 24 during insertion and retraction or removal of the bur 50. In this embodiment, the ram 40 is mounted in the casing sleeve 30 at the tool insertion end 13 of the drive spindle 10 axially aligned with and adjacent to the chuck 20. The ram 40 and has a central tool opening 42 for passage of the bur 50 and a pair of diametrically opposed lugs 44 extending axially from the ram 40 towards the chuck 20 in the assembled condition of the spindle 10. The lugs 44 are shaped to engage the axial slits 26 of the chuck 20 in the assembled condition. The lugs 44 are longitudinally tapered to force apart the retaining arms 24 when the ram 40 and chuck 20 are forced towards one another. The ram 40 is preferably fastened to the casing sleeve 30 and the chuck 20 is preferably movable in the casing sleeve 30 to allow for movement of the chuck 20 relative to the ram 40, for use of the spindle 10 in pushbutton release handpieces. Activating the pushbutton of such a handpiece (not illustrated) will move the chuck 20 in the casing sleeve 30 toward the ram 40 whereby the retaining arms 24 are radially forced apart by the lugs 44, as will be readily apparent to the person skilled in the art. The ram 40 is permanently or releasably fastened to the casing sleeve 30 by a threaded connection or a press-fit. Other possible fastening methods include welding or gluing. However, the fastening method used must ensure that the ram 40 will not move relative to the casing sleeve 30 when the ram and chuck are forced against one another for the opening of the retaining arms 24.

Figure 6A:
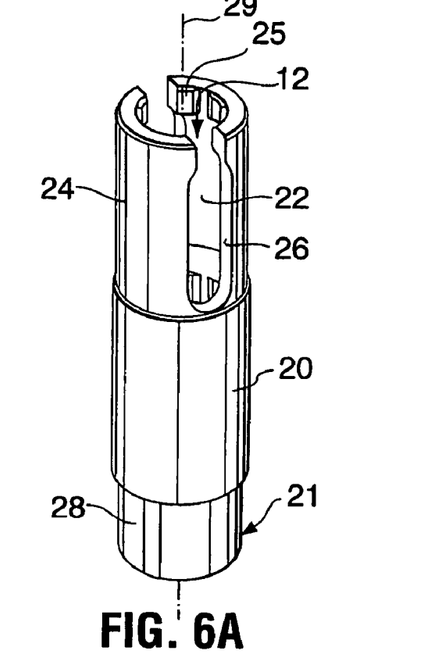
FIGS. 6A and 6B illustrate perspective front and rear end views of a preferred embodiment of a chuck of the tool supporting element aspect of the present invention.
Figure 6B:
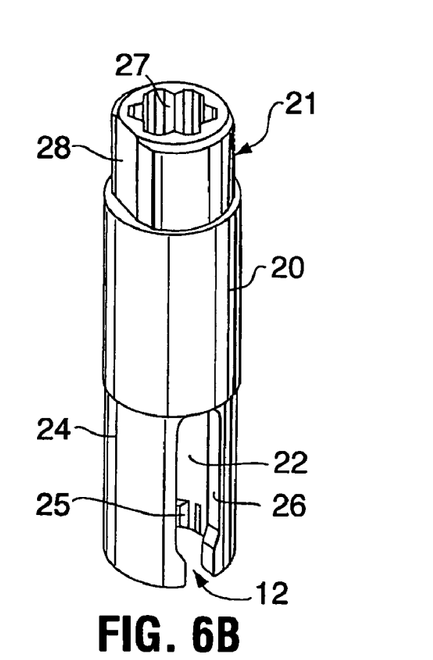
Figure 7:
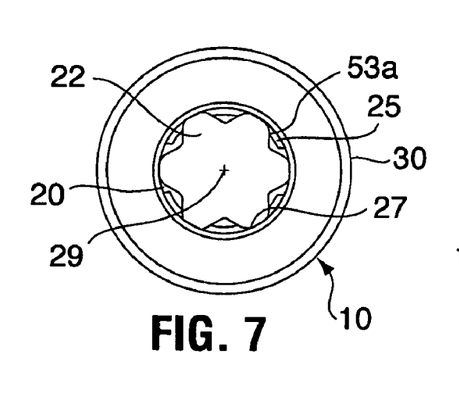
FIG. 7 illustrates an end view from the tool receiving end of the drive spindle of FIG. 2, but shown in assembled condition.

In one variant of the spindle 10, the casing sleeve 30 represents the torque receiving element of the spindle. The sleeve 30 fits sufficiently closely into the spindle socket 109 of the drive head 101 (see FIG. 1) to ensure reliable torque transfer from the drive 105 to the spindle 10. Rotational torque is then transferred from the spindle 10 to the bur 50 through engagement of the lugs 44 of the ram 40 in the axial slits 26 of the chuck 20 and frictional engagement of the retaining arms 24 with the contact surface 60 on the bur 50. In another variant of the spindle 10 as shown in FIGS. 6A and 6B, torque is transferred directly from the drive 105 to the chuck 20 by way of a torque key 28 on the driven chuck end 21 of the chuck, which is shaped for fitting engagement with a torque socket (not illustrated) at a bottom of the spindle socket 109. The torque key 28 is formed by providing the driven chuck end 21 with any non-circular outer cross-section. The torque key 28 and the torque socket preferably have complementary shapes, but non-complementary shapes providing an interference fit can also be used as long as rotation of the torque key 28 in the torque socket is reliably prevented. In a preferred embodiment, the non-circular torque key 28 is shaped from a generally cylindrical end portion of the chuck 20 which is provided with two diametrically opposed flattened surface portions.

Figure 4:
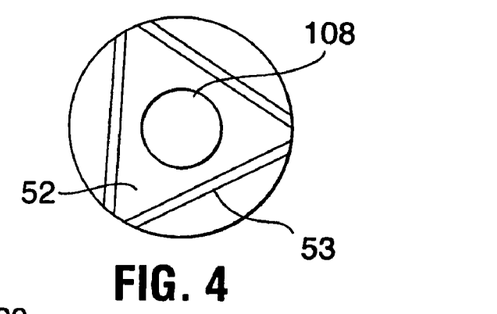
FIG. 4 is an axial end view of the dental bur shown in FIG. 3D illustrating a torque lock.
Figure 8:
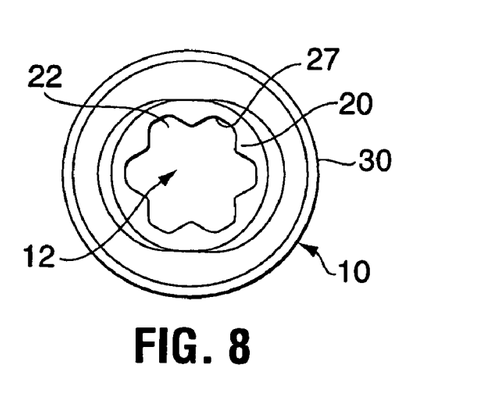
FIG. 8 illustrates an end view from the driven end of the drive spindle of FIG. 7.

In a preferred embodiment of the drive arrangement, the drive arrangement further includes a structure for locking the bur 50 against rotation in the tool passage 12 of the drive spindle 10. This unique torque transfer arrangement is preferably combined with the torque key and torque socket arrangement described directly above to provide for direct torque transfer from the drive 105 to the bur 50 without the possibility of any slippage and the associated heat generation and possible thermal damage to components of the drive arrangement, especially the tempered tool retaining arms 24. The torque transfer arrangement includes a locking portion 53 on the bur 50, which has an outer non-circular cross section (see FIGS. 3D, 4 to 8, 10, 11) and a locking socket 27 in the chuck 20, which has a complementary or interlocking cross-section. The locking portion 53 is shaped to slidably fit into the locking socket 27 to allow length adjustment of the bur 50 by retracting the bur 50 from the fully inserted position in accordance with the principle aspect of the invention. Preferably, the locking socket 27 is co-extensive with the first tool seat 14, which means the first tool seat 14 is shaped as a locking socket of a cross-sectional shape permitting fitting and slidable insertion of the locking portion 53 of the bur 50 while positively preventing rotation of the locking portion 53 in the locking socket 27. FIG. 4 shows an axial end view of a preferred embodiment of a dental bur 50 in accordance with the present invention having a locking portion 53 of triangular cross-section. FIG. 8 illustrates an end view of the drive spindle 10 of the preferred embodiment of FIG. 2, illustrating the cross-sectional shape of the locking socket 27 which is not directly complementary to the cross-section of the locking portion 53 shown in FIG. 4, but nevertheless provides an interference fit of the locking portion 53 in the looking socket 27 to guarantee a reliably interlocking between the locking portion 53 and the locking socket 27. The locking socket 27 is multi-faceted socket formed in a portion of the tool passage 12 of the chuck 20 near the driven end 21 of the chuck. The multi-faceted locking socket 27 provides multiple possible insertion orientations for the triangular lock portion 53 to improve the chance of aligning the locking portion 53 with the locking socket 27 without the aid of visual pre-alignment.

In a particularly preferred embodiment, the locking socket 27 extends substantially the whole length of the tool passage 12 for maintaining concentricity during rotation. It is preferable that the locking portion 53 and the locking socket be rotation symmetrical, which means symmetrical about the axis of rotation to prevent excessive vibration of the bur 50/chuck 20 and, thus the handpiece during high speed rotation. In the alternative, the locking portion 53 and/or the locking socket 27 can also be momentum symmetrical, which means weight balanced about the axis of rotation, again to prevent excessive vibration in the handpiece.

To improve the ease of proper alignment of the locking portion 53 with the locking socket 27, a particularly preferred embodiment of the chuck 20 includes a bur aligning member 53a (see FIG. 7) near the bur insertion end of the drive spindle 10. The bur aligning member 53a preferably corresponds in shape and orientation with the non-circular locking socket 27, which is generally located deep in the drive head of the handpiece. This bur aligning member 53a allows for pre-alignment of the locking portion 53 with the locking socket 27 upon insertion of the driven portion 54 into the drive spindle 10. The bur aligning member 53a preferably forms part of the tool engaging tab 25 as shown in FIG. 6.

Figure 12:
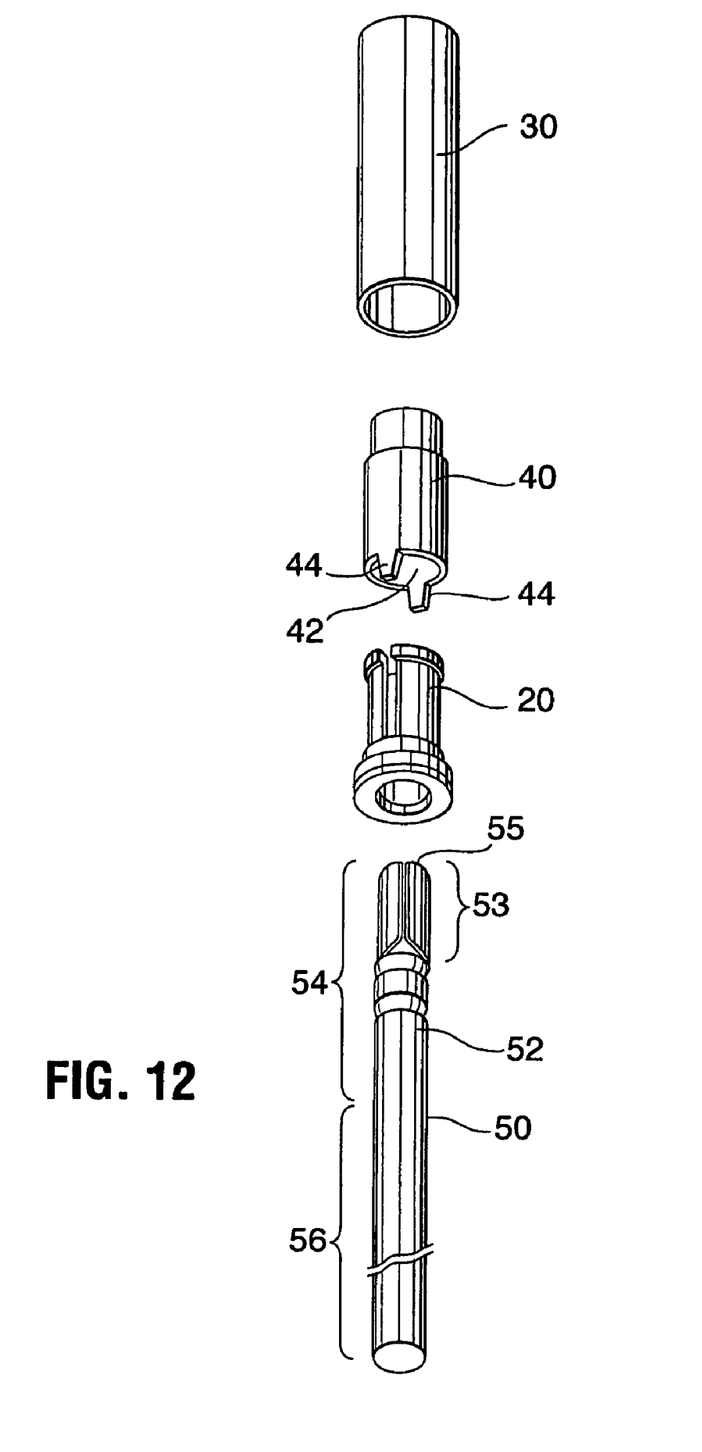
FIG. 12 illustrates an alternative preferred embodiment of the drive spindle of FIG. 2.

In the alternate embodiment shown in FIG. 12, all parts perform the same function, although the chuck 20 and ram 40 are positioned in the spindle 10 in an axially opposite orientation to that in the embodiment of FIG. 2. The bur 50 is inserted first into the chuck 20 and subsequently enters the axially aligned and adjacent ram 40. The ram is in communication with the drive mechanism in the handpiece for receiving drive torque by way of the torque key 28 similar to the one on the chuck 20 of the embodiment shown in FIG. 2. The ram 40 engages the chuck 20 in a torque transfer arrangement thereby to rotatably drive the bur 50. In the variant illustrated in FIG. 12, drive torque is transferred through the lugs 44 engaged with the axial slits 26. The torque is then transferred from the chuck 20 to the bur 50, by way of friction between the bur and the diametrically opposed axial retaining arms 24.

The locking socket (not shown) in this alternate preferred embodiment is located within the tool-receiving bore of the ram 40. The locking socket is preferably elongated and radially supports the bur 50 to maintain concentricity during rotation at various insertion depths between $D_{min}$ and $D_{max}$. The socket is complementary in shape to the non-circular cross-sectional locking portion 53 of the bur 50.

Other non-circular cross-sectional lock portions and complementary locking sockets are also contemplated, for example, square-, rectangle-, octagonal-, diamond-, star-, and flattened circle-shaped among others. A non-circular locking portion can also have a generally circular shape with one or more indents, notches or axial grooves projecting radially inwardly into the locking portion 53. A variant in which the locking portion 53 of the bur 50 directly engages a locking socket 27 formed in a portion of the drive mechanism, for example a turbine, for direct torque transfer is also contemplated. It is contemplated that a dental tool in accordance with the present invention can have any type of working tip for contacting a tooth surface known in the art. Furthermore, a portion or all of the tool may be provided with a wear resistant coating. One or more of the components of the rotatable tool drive arrangement of the present invention may be provided with a low friction coating, for example the lugs 44 of the ram 40. It is contemplated that a tool according to the present invention may comprise an axial channel to allow passage of air or liquid from the handpiece to a surface of a tooth. It is also contemplated that the tool of the invention may be a tool other than a dental bur.

The above-described embodiments of the present invention are intended to be examples only. Alterations, modifications and variations may be effected to the particular embodiments by those of skill in the art without departing from the scope of the invention, which is defined solely by the claims appended hereto.

What is claimed is:

1. A rotatable tool drive assembly for use with a dental handpiece including a drive head producing rotational torque, the rotatable tool drive assembly comprising:
    a rotatable tool including a tool body having a driven portion with a driven end and a working portion with a working end;
    a sleeve adapted for insertion into the drive head and receiving rotational torque therefrom;
    a chuck disposed in the sleeve and movable axially relative thereto, the chuck extending between a driven chuck end and a tool receiving end, the chuck including a tool passage receiving the driven portion of the rotatable tool therein, the driven chuck end defining a first tool seat concentrically supporting the driven end of the rotatable tool, the tool receiving end including at least two retaining arms engaging the driven portion of the rotatable tool and releasably retaining the rotatable tool against axial movement; and
    a ram secured to the sleeve directly adjacent the tool receiving end of the chuck, the ram having a central tool opening receiving the driven portion of the rotatable tool therein, the ram defining a second tool seat axially spaced apart from the first tool seat concentrically supporting the driven portion of the rotatable tool at a location intermediate the driven end and the working portion, the ram including at least two lugs extending axially towards the tool receiving end of the chuck, the at least two lugs adapted for engaging the chuck causing the at least two retaining arms to disengage with the driven portion of the rotatable tool in response to moving the chuck toward the ram;
    wherein the first tool seat being axially elongated and concentrically supporting the driven end of the rotatable tool at any position from a maximum insertion depth wherein the rotatable tool is fully inserted into the chuck to a maximum retraction depth wherein the rotatable tool is retracted from the maximum insertion depth and the driven end is still engaged in the first tool seat.

2. The rotatable tool drive assembly of claim 1, wherein the tool receiving end of the chuck includes a pair of axial slits and the at least two retaining arms is a pair of diametrically opposite retaining arms, the pair of retaining arms engaging the driven portion of the rotatable tool and releasably retaining the rotatable tool against axial movement.

3. The rotatable tool drive assembly of claim 2, wherein the at least two lugs of the ram is a pair of lugs adapted for engaging the pair of axial slits causing the pair of retaining arms to disengage with the driven portion of the rotatable tool in response to moving the chuck toward the ram.

4. The rotatable tool drive assembly of claim 3, wherein the rotatable tool includes a maximum retraction indicator indicating to a user when the rotatable tool has been retracted to the maximum retraction depth.

5. The rotatable tool drive assembly of claim 4, wherein the rotatable tool includes a maximum insertion indicator indicating to a user when the rotatable tool has been inserted to the maximum insertion depth.

6. The rotatable tool drive assembly of claim 5, wherein the maximum insertion and retraction depth indicators are annular grooves in the driven portion of the rotatable tool for mechanical engagement by the pair of retaining arms, an axial spacing of the grooves being no greater than the axial length of the first tool seat.

7. The rotatable tool drive assembly of claim 1, wherein the rotatable tool further includes a torque lock portion of non-circular cross-section positioned at the driven end of the rotatable tool and the first tool seat includes a locking socket of a cross-section complementary to the torque lock portion of the rotatable tool.

8. A rotatable tool drive assembly having a first axis of rotation for use with a dental handpiece including a drive head having a drive producing rotational torque, the rotatable tool drive assembly comprising:

a rotatable tool including a tool body having a second axis of rotation coaxial with the first axis of rotation, the tool body having a driven portion with a driven end and a working portion with a working end;

a sleeve adapted for insertion into the drive assembly;

a chuck disposed in the sleeve and movable axially relative thereto, the chuck extending between a driven chuck end and a tool receiving end, the chuck including a tool passage receiving the driven portion of the rotatable tool therein, the driven chuck end including a torque key adapted for fitting engagement with the drive and receiving rotational torque therefrom, the driven chuck end defining a first tool seat concentrically supporting the driven end of the rotatable tool, the tool receiving end including at least two retaining arms engaging the driven portion of the rotatable tool and releasably retaining the rotatable tool against axial movement; and a ram secured to the sleeve directly adjacent the tool receiving end of the chuck, the ram having a central tool opening receiving the driven portion of the rotatable tool therein, the ram defining a second tool seat axially spaced apart from the first tool seat concentrically supporting the driven portion of the rotatable tool at a location intermediate the driven end and the working portion, the ram including at least two lugs extending axially towards the tool receiving end of the chuck, the at least two lugs adapted for engaging the chuck causing the at least two retaining arms to disengage with the driven portion of the rotatable tool in response to moving the chuck toward the ram;

wherein the first tool seat being axially elongated and concentrically supporting the driven end of the rotatable tool at any position from a maximum insertion depth wherein the rotatable tool is fully inserted into the chuck to a maximum retraction depth wherein the rotatable tool is retracted from the maximum insertion depth and the driven end is still engaged in the first tool seat.

9. The rotatable tool drive assembly of claim 8, wherein the tool receiving end of the chuck includes a pair of axial slits and the at least two retaining arms is a pair of diametrically opposite retaining arms, the pair of retaining arms engaging the driven portion of the rotatable tool and releasably retaining the rotatable tool against axial movement.

10. The rotatable tool drive assembly of claim 9, wherein the at least two lugs of the ram is a pair of lugs adapted for engaging the pair of axial slits causing the pair of retaining arms to disengage with the driven portion of the rotatable tool in response to moving the chuck toward the ram.

11. The rotatable tool drive assembly of claim 10, wherein the rotatable tool includes a maximum retraction indicator indicating to a user when the rotatable tool has been retracted to the maximum retraction depth.

12. The rotatable tool drive assembly of claim 11, wherein the rotatable tool includes a maximum insertion indicator indicating to a user when the rotatable tool has been inserted to the maximum insertion depth.

* * * * *